United States Patent [19]

Hara et al.

[11] Patent Number: 5,316,767
[45] Date of Patent: May 31, 1994

[54] WHITENING COSMETIC COMPOSITION

[75] Inventors: Takahiro Hara, Machida; Seigo Takasawa, Hatano; Yoshiharu Yokoo, Sagamihara, all of Japan; Tadayasu Furukawa, Chesterfield, Mo.

[73] Assignee: Kyowa Hakko Kogyo Co., Ltd., Japan

[21] Appl. No.: 985,535

[22] Filed: Dec. 3, 1992

Related U.S. Application Data

[63] Continuation of Ser. No. 765,624, Sep. 25, 1991, abandoned.

[30] Foreign Application Priority Data

Sep. 28, 1990 [JP] Japan .................. 2-259384

[51] Int. Cl.$^5$ .............................................. A61K 6/00
[52] U.S. Cl. ...................................... 424/401; 424/63
[58] Field of Search ................... 424/401, 62, 60; 530/330, 331, 332; 514/724

[56] References Cited

U.S. PATENT DOCUMENTS

| | | | |
|---|---|---|---|
| 4,419,343 | 12/1983 | Pauly | 424/59 |
| 4,812,307 | 3/1989 | Siuta-Mangano | 424/71 |
| 4,927,808 | 5/1990 | Kitahara et al. | 530/330 |
| 4,959,393 | 9/1990 | Torihara et al. | 514/724 |
| 4,990,330 | 2/1991 | Oyama | 424/60 |

FOREIGN PATENT DOCUMENTS

| | | |
|---|---|---|
| 0010483 | 4/1980 | European Pat. Off. . |
| 0299764 | 1/1989 | European Pat. Off. . |
| 2245903 | 3/1973 | Fed. Rep. of Germany . |
| 2932923 | 2/1981 | Fed. Rep. of Germany . |
| 2608425 | 6/1988 | France . |
| 48-01506 | 1/1973 | Japan . |
| 48-29139 | 9/1973 | Japan . |
| 49-035417 | 9/1974 | Japan . |
| 53-003538 | 1/1978 | Japan . |
| 53-006432 | 1/1978 | Japan . |
| 55-111410 | 8/1980 | Japan . |
| 55-111411 | 8/1980 | Japan . |
| 57-134410 | 8/1980 | Japan . |
| 55-157580 | 8/1980 | Japan . |
| 55-092305 | 12/1980 | Japan . |
| 56-079616 | 6/1981 | Japan . |
| 57-014517 | 1/1982 | Japan . |
| 58-022151 | 5/1983 | Japan . |
| 58-131911 | 6/1983 | Japan . |
| 59-157009 | 9/1984 | Japan . |
| 60-016906 | 1/1985 | Japan . |
| 60-056912 | 2/1985 | Japan . |
| 61-18926 | 8/1986 | Japan . |
| 63-188618 | 8/1988 | Japan . |
| 63-267711 | 11/1988 | Japan . |
| 01044709 | 2/1989 | Japan . |
| 1256586 | 10/1989 | Japan . |
| 2134309 | 5/1990 | Japan . |
| WO86/05783A | 10/1986 | PCT Int'l Appl. . |
| 2052973 | 2/1981 | United Kingdom . |

OTHER PUBLICATIONS

European Search Report for corresponding application EP 91308743.3, issued Feb. 17, 1992.
Anderson, M. E. et al., Proc. Natl. Acad. Sci. USA 80:707–711 (1983).
Meister, A. et al., Ann. Rev. Biochem. 52:711–713 (1983).
Anderson, M. E. et al., Meth. Enzymol. 113:555–564 (1985).
Reitman, J. S. et al., Biochim. Ciophys. acta 208:159–162 (1970).

*Primary Examiner*—Thurman K. Page
*Assistant Examiner*—William E. Benston, Jr.
*Attorney, Agent, or Firm*—Pennie & Edmonds

[57] ABSTRACT

Disclosed is a whitening cosmetic composition comprising γ-L-glutamyl-L-cystine, γ-L-glutamyl-L-cysteine disulfide, oxidized glutathione or a derivative thereof, the amino group of which is acylated with an alkanoyl group or an aroyl group. The whitening cosmetic composition of the present invention have extremely good in water solubility and heat stability and stability during storage and show a melanin formation inhibitory activity against melanoma cells without any cytotoxicity.

8 Claims, 1 Drawing Sheet

WHITENING COSMETIC COMPOSITION

This is a continuation of application 07/765,624, filed Sep. 25, 1991, now abandoned.

BACKGROUND OF THE INVENTION

The present invention relates to a cosmetic composition comprising γ-L-glutamyl-L-cystine, γ-L-glutamyl-L-cysteine disulfide, oxidized glutathione or a derivative thereof, the amino group of which is acylated with an alkanoyl group or an aroyl group.

Cosmetics have hitherto been developed for the purpose of preventing blackening of the skin caused by sunburn/suntan or for the prevention or treatment for pigmentation such as stains of freckles.

Glutathione (γ-L-glutamyl-L-cysteinyl-glycine) is inherently present in vivo. It is known to formulate glutathione in cosmetics or external remedies.

Various formulations of glutathione derivatives in cosmetics have also been known (Japanese Published Examined Patent Application Nos. 1505/73 and 29139/73, WO 86/05783, Ger. offen. 2245903).

With respect to oxidized glutathione, a hair modifying composition comprising the same compound and the like are known (Japanese Published Unexamined Patent Application No. 188618/88, U.S. Pat. No. 4,812,307, European Patent Application No. 299,764).

It is also known to formulate kojic acid or arbutin in cosmetics (Japanese Published Examined Patent Application No. 18569/81 and Japanese Published Unexamined Patent Application No. 16906/85). But kojic acid and arbutin are unstable and slightly soluble in water and they can not effectively prevent blackening of the skin caused by sunburn/suntan.

Further, it is difficult to formulate glutathione in cosmetics because of its unstableness and offensive odor.

It has been desired to develop whitening cosmetics which are stable to heat and light, free of toxicity and skin damages, and can be used safely.

SUMMARY OF THE INVENTION

The present invention provides a whitening cosmetic composition comprising γ-L-glutamyl-L-cystine, γ-L-glutamyl-L-cysteine disulfide, oxidized glutathione or a derivative thereof, the amino group of which is acylated with an alkanoyl group or an aroyl group.

DETAILED DESCRIPTION OF THE INVENTION

Figure 1:
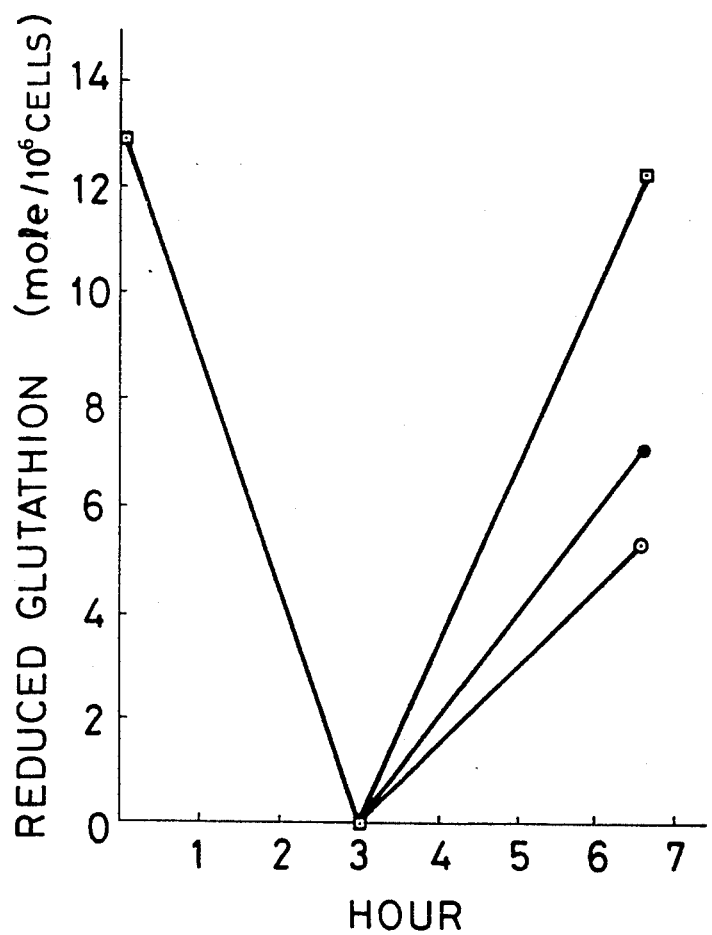

Structural formulas of γ-L-glutamyl-L-cystine, γ-L-glutamyl-L-cysteine disulfide, oxidized glutathione are given below:

γ-L-glutamyl-L-cystine:

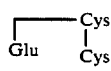

γ-L-glutamyl-L-cysteine disulfide:

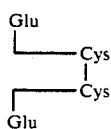

oxidized glutathione:

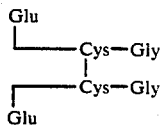

Examples of the alkanoyl group in the derivative, the amino group of which is acylated with an alkanoyl group or an aroyl group include a straight or branched saturated or unsaturated alkanoyl group containing 1 to 20 carbon atoms, and examples of the aroyl group include benzoyl, naphthoyl, etc.

These compounds are extremely stable and maintain their high stability even when they are incorporated in cosmetics. For example, as shown in Table 1 described below, the compounds do not decompose by a heat treatment at 100° C. for 20 minutes at pH 6.5 in a concentration of 10 mM. Even though these compounds are allowed to stand at pH 6.5 in a concentration of 10 mM at 40° C. for 30 days, no decomposition occurs. In this case, no unpleasant smell is given off at all, but kojic acid is colored.

TABLE 1

| Test Compound | Residual rate after heating at 100° C. for 20 minutes (%) | Residual rate after allowing to stand at 40° C. for 30 days (%) |
|---|---|---|
| γ-L-glutamyl-L-cystine | 100 | 100 |
| γ-L-glutamyl-L-cysteine disulfide | 100 | 100 |
| Oxidized glutathione | 100 | 100 |
| N,N'-diacetyl-oxidized glutathione | 100 | 100 |
| Arbutin | 100 | 100 |
| Kojic acid | 100 | 100 |
| Glutathione | 70 | 0 |

(※ 10 mM concentration, pH 6.5)

Furthermore, γ-L-glutamyl-L-cystine, γ-L-glutamyl-L-cysteine disulfide, oxidized glutathione and N,N'-diacetyl-oxidized glutathione have markedly high water solubility as compared with that of arbutin or kojic acid, as shown in Table 2.

TABLE 2

| Test Compound | Solubility (g/l) |
|---|---|
| γ-L-glutamyl-L-cystine | >742.2 |
| γ-L-glutamyl-L-cysteine disulfide | >554.4 |
| Oxidized glutathione | >320.0 |
| N,N'-diacetyl-oxidized glutathione | >200 |
| Arbutin | 141.6 |
| Kojic acid | 48.3 |

(pH not adjusted, 25° C.)

Since γ-L-glutamyl-L-cystine is converted into glutathione in vivo glutathione level can be improved. As a result, whitening effect of the cosmetic can be supposed to be exhibited.

Hereafter, the activity for recovering glutathione level of γ-L-glutamyl-L-cystine in fibroblast is explained by referring to Experiment 1.

Experiment 1

A glutathione level in cells was reduced by an agent for glutathione depletion, diethyl maleate, and the agent was then removed. In this case, the activity for recovering glutathione level of γ-L-glutamyl-L-cystine in cells was compared according to the following method, using a glutathione-added group and a group with nothing added as a control.

Method

After 2 ml of MEM medium (manufactured by Nissui Pharmaceutical Co.) (serum concentration of 5%) was added in a 6-well culture plate, mouse-derived L929 fibroblast was plated at $2 \times 10^5$ cells/well and cultured at 37° C. for 3 days in 5% $CO_2$ incubator. 100 μM of diethyl maleate (manufactured by Sigma Co.) was added to the culture medium and glutathione in the cells was depleted by culturing for further 3 hours.

Diethyl maleate was removed by discarding the culture medium. Then, 2 ml of fresh MEM medium was added and γ-L-glutamyl-L-cystine or glutathione was added in a concentration of 1 mM. After incubation at 37° C. for 3.5 hours in 5% $CO_2$ incubator, the cells were trypsinized and resuspended in phosphate buffer solution (PBS) and a cell count was determined. A glutathione level in the cells was determined by treating the cells with 4.5% trichloroacetic acid/16 mM ethylenediaminetetraacetic acid (EDTA), extracting an acid-soluble fraction, and then the fraction was analyzed by high performance liquid chromatography* (HPLC).

* HPLC [monochloroacetic acid-acetonitrile (96:4 containing 5 mM sodium 1-octanesulfonate); column: BIOPHASE ODS II (B.A.S. Co.), 250×4.6 mmφ; 1 ml/min]

The results are shown in FIG. 1.

FIG. 1 indicates the results of a test on glutathione level recovery in L929 fibroblast. In the FIGURE, the coordinate shows a reduced glutathione (GSH) level per $10^6$ cells and the abscissa shows time, in which, □, and ● designate the group with added glutathione, the group with added γ-L-glutamyl-L-cystine and an intact group for control, respectively.

As shown in FIG. 1, γ-L-glutamyl-L-cystine could significantly increase the glutathione level in the cells, which had been reduced by diethyl maleate, as compared with the non-addition group, although this compound is inferior to glutathione.

γ-L-glutamyl-L-cysteine disulfide, oxidized glutathione and the derivative thereof, the amino group of which is acylated with an alkanoyl group or an aroyl group, have an activity of inhibiting melanin formation in melanoma cells. It is thus expected that the utility of these compounds as whitening cosmetics would be attributable to the melanin formation inhibitory activity.

The melanin formation inhibitory activity of γ-L-glutamyl-L-cysteine disulfide, oxidized glutathione and the derivative thereof, the amino group of which is acylated with an alkanoyl group or an aroyl group, N,N'-diacetyl oxidized glutathione, in melanoma cells is explained with reference to Experiment 2.

Experiment 2

Method

The melanin formation inhibitory activity of the γ-L-glutamyl-L-cysteine disulfide, oxidized glutathione and N,N'-diacetyl oxidized glutathione in melanoma cells were compared by the following method, using groups with added arbutin, kojic acid and nothing as control.

After 2 ml of MEM medium (manufactured by Nissui Pharmaceutical Co.) (serum concentration of 5%) was added in a 6-well culture plate, mouse-derived B16-C melanoma cells were plated at $2 \times 10^5$ cells/well and test compounds were then separately added. B16-C melanoma cells were cultured at 37° C. in 5% $CO_2$ incubator. On Day 3 and Day 5, the medium was exchanged and at the same time, the test compounds were separately added. On Day 7, the medium was removed. The cells were trypsinized and resuspended in PBS and pelleted by centrifugation. The cells were treated with 10% trichloroacetic acid and the acid-soluble fraction was removed. The precipitated acid-insoluble fraction was solubilized with an alkali solution (1N sodium hydroxide/10% dimethylsulfoxide) in order to make a test solution. The protein content in the cells and the amount of melanin formed were determined, whereby the amount of melanin formed (μg) per protein content (mg) were calculated.

The protein content and the amount of melanin formed were quantitatively determined by the method of Bradford et al. [Analytical Biochemistry, 72, 248–254 (1976)] and by measuring absorbance of the test solution at 470 nm [Cancer Research, 45, 1474–1478 (1985)], respectively.

The results are shown in Table 3.

TABLE 3

| Test Compound | Concentration (mM) | Melanin Content/Protein Content (μg/mg) |
|---|---|---|
| Nothing added | — | 211.4 ± 11.45 |
| GSSG*1 | 0.5 | 158.3 ± 15.2 |
|  | 1.0 | 139.2 ± 9.52 |
|  | 2.0 | 141.1 ± 6.73 |
| GCCG*2 | 0.5 | 189.3 ± 10.56 |
|  | 1.0 | 155.6 ± 7.68 |
|  | 2.0 | 154.7 ± 12.16 |
| Arbutin | 0.25 | 108.7 ± 13.04 |
|  | 0.5 | 89.2 ± 13.48 |
|  | 1.0 | growth inhibition |
| Kojic acid | 0.25 | 233.7 ± 14.37 |
|  | 0.5 | 202.4 ± 11.49 |
|  | 1.0 | 188.6 ± 9.93 |
| Nothing added | — | 330.1 ± 22.5 |
| N,N'-GSSG*3 | 1.0 | 221.4 ± 18.6 |
|  | 2.0 | 198.1 ± 8.5 |
| GSSG | 1.0 | 229.1 ± 13.4 |
|  | 2.0 | 225.9 ± 25.3 |

*1GSSG designates oxidized glutathione.
*2GCCG designates γ-L-glutamyl-L-cysteine disulfide.
*3N,N'-GSSG designates N,N'-diacetyl oxidized glutathione.

As shown in Table 3, it was confirmed that the γ-L-glutamyl-L-cysteine disulfide, oxidized glutathione and N,N'-diacetyl oxidized glutathione showed the activity of significantly inhibiting melanin formation in B16-C melanoma cells. The activity of kojic acid for inhibiting melanin formation was poorer than those of γ-L-glutamyl-L-cysteine disulfide and oxidized glutathione.

Furthermore, with respect to γ-L-glutamyl-L-cysteine disulfide, oxidized glutathione and N,N'-diacetyl oxidized glutathione, no cytotoxicity such as death of cells, etc. was recognized even in a concentration of 2 mM. However, arbutin showed cytotoxicity in a concentration of 1 mM.

γ-L-glutamyl-L-cystine, γ-L-glutamyl-L-cysteine disulfide and oxidized glutathione, which are used in the present invention, can be synthesized by the method described in Methods in Enzymology [113, 554–564 (1985)].

N,N'-diacetyl oxidized glutathione can be synthesized by the method described in Biochim. Biophys. Acta, [208, 159–162 (1970)].

In the present invention, the γ-L-glutamyl-L-cystine, γ-L-glutamyl-L-cysteine disulfide, oxidized glutathione and the derivative thereof, the amino group of which is acylated with an alkanoyl group or an aroyl group, are employed in the composition in an amount of 0.001 to 10 W/W %.

The cosmetically acceptable components are fats and oils, hydrocarbons, waxes, fatty acids, synthetic esters, alcohols, surfactants, thickeners, moisturizers, preservatives, fragrance, pigments, chemicals and purified water which are conventionally used in cosmetics.

Examples of the fats and oils include jojoba oil, castor oil, olive oil, soybean oil, coconut oil, palm oil, cacao butter, mink oil, turtle oil, coconut oil and fatty acid diethanolamide.

Examples of the hydrocarbons include liquid paraffin, vaseline, microcrystalline wax and squalane.

Examples of the waxes include beeswax, lanoline, carnauba wax and candelilla wax.

Examples of the fatty acids include myristic acid, palmitic acid, stearic acid, oleic acid and isostearic acid.

Examples of the synthetic esters include isopropyl myristate, isopropyl palmitate, butyl oleate, myristyl myristate, octyldecyl myristate, propyleneglycol monostearate, myristyl lactate isostearyl malate, glycerine monostearate and distearyldimethyl ammonium chloride.

The fats and oils, hydrocarbons, waxes, fatty acids and synthetic esters are usually employed in the composition in an amount of 0.1 to 30 W/W % collectively.

Examples of the alcohols include ethanol, 1,3-butylene glycol, propylene glycol, lauryl alcohol, cetanol, stearyl alcohol and oleyl alcohol. The alcohols are employed in the composition in an amount of 0.1 to 25 W/W %.

Examples of the surfactants include polyoxyethylene-hardened castor oil, sodium lauryl sulfate, polyoxyethyleneglyceryl pyroglutamate isostearate, sodium alkylbenzenesulfonate, polyoxyethylene (10) stearyl ether, dialkyl sulfosuccinate, cetyl pyridinium bromide, n-octadecyl trimethylammonium chloride, monoalkyl phosphate, N-acylglutamic acid, sucrose fatty acid ester, polyoxyethylene (20) sorbitan monostearate, sodium polyoxyethylene lauryl ether sulfate and polyoxyethylene-reduced lanoline.

The surfactants are usually employed in the composition an amount of 0.1 to 5 W/W %.

Examples of the thickeners include carboxyvinyl polymer, methylpolysiloxane, dextran, carboxymethyl cellulose, carrageenan and hydroxypropyl methyl cellulose.

The thickeners are usually employed in the composition in an amount of 0.01 to 0.5 W/W %.

Examples of the moisturizers include glycerine, propylene glycol, 1,3-butylene glycol, pyrrolidone-carboxylic acid, lactic acid and hyaluronic acid. The moisturizers are employed in the composition in an amount of 0.01 to 25 W/W %.

Examples of the preservatives include benzoic acid, salicylic acid, dehydroacetic acid or salts thereof, phenols such as p-oxybenzoic acid ester, 3-trifluoromethyl-4,4'-dichlorocarbanilide, 2,4,4'-trichloro-2'-hydroxydiphenyl ether. The preservatives are employed in the composition in an amount of 0.01 to 0.3 W/W %.

Any fragrance may be used so long as it is conventionally used in cosmetics.

Examples of the pigments include iron oxide, titanium dioxide, zinc oxide, kaolin and talc. The pigments are employed in the composition in an amount of 0.01 to 1 W/W %.

Examples of the chemicals include wheat germ oil, vitamin E, vitamin A, vitamin B2, magnesium ascorbic acid-2-phosphate, D-pantothenyl alcohol and dipotassium glycyrrhizinate. The chemicals are employed in the composition in an amount of 0.01 to 5 W/W %.

The cosmetic composition of the present invention may take any form of soluble system, emulsion type, dispersion system, and the like.

As cosmetic preparation of the present invention, there are, for example, a lotion, a cream, an emulsion, a pack composition, a powder, etc.

The present invention is described below by referring to examples.

EXAMPLE 1

A lotion having the following composition was prepared.

Composition 1

| | |
|---|---|
| (1) $\gamma$-L-glutamyl-L-cystine | 0.1 g |
| (2) Propylene glycol | 3.0 g |
| (3) Sodium pyrrolidonecarboxylate | 0.3 g |
| (4) Methylparaben | 0.1 g |
| (5) Polyoxyethylene polyoxypropylene alkyl ether | 1.0 g |
| (6) Ethanol | 10.0 g |
| (7) Fragrance | suitable quantity |
| (8) Purified water | suitable quantity |
| | 100.0 g in total |

Method of Preparation

The aqueous layer ingredients (1) to (4) and (8) were mixed and dissolved under heating at 60° C. Then, the oily layer ingredients (5) to (7) mixed and dissolved were added to the solution. The mixture was stirred to make a homogeneous mixture. And the mixture was cooled and filtered to make a lotion.

EXAMPLE 2

A lotion having the following composition was prepared.

Composition 2

| | |
|---|---|
| (1) $\gamma$-L-glutamyl-L-cysteine disulfide | 0.1 g |
| (2) Propylene glycol | 3.0 g |
| (3) Sodium pyrrolidonecarboxylate | 0.3 g |
| (4) Methylparaben | 0.1 g |
| (5) Polyoxyethylene polyoxypropylene alkyl ether | 1.0 g |
| (6) Ethanol | 10.0 g |
| (7) Fragrance | suitable quantity |
| (8) Purified water | suitable quantity |
| | 100.0 g in total |

Method of Preparation

A lotion was obtained by effecting mixing and treatment in accordance with the formulation similar to that of Example 1 except that $\gamma$-L-glutamyl-L-cysteine disulfide was used instead of $\gamma$-L-glutamyl-L-cystine.

EXAMPLE 3

A lotion having the following composition was prepared.

Composition 3

| | | |
|---|---|---|
| (1) | Oxidized glutathione | 0.1 g |
| (2) | Propylene glycol | 3.0 g |
| (3) | Sodium pyrrolidonecarboxylate | 0.3 g |
| (4) | Methylparaben | 0.1 g |
| (5) | Polyoxyethylene polyoxypropylene alkyl ether | 1.0 g |
| (6) | Ethanol | 10.0 g |
| (7) | Fragrance | suitable quantity |
| (8) | Purified water | suitable quantity |
| | | 100.0 g in total |

Method of Preparation

A lotion was obtained by effecting mixing and treatment in accordance with the formulation similar to that of Example 1 except that oxidized glutathione was used instead of γ-L-glutamyl-L-cystine.

EXAMPLE 4

A lotion having the following composition was prepared.

Composition 4

| | | |
|---|---|---|
| (1) | N,N'-diacetyl oxidized glutathione | 0.1 g |
| (2) | Propylene glycol | 3.0 g |
| (3) | Sodium pyrrolidonecarboxylate | 0.3 g |
| (4) | Methylparaben | 0.1 g |
| (5) | Polyoxyethylene polyoxypropylene alkyl ether | 1.0 g |
| (6) | Ethanol | 10.0 g |
| (7) | Fragrance | suitable quantity |
| (8) | Purified water | suitable quantity |
| | | 100.0 g in total |

Method of Preparation

A lotion was obtained by effecting mixing and treatment in accordance with the formulation similar to that of Example 1 except that N,N'-diacetyl oxidized glutathione was used instead of γ-L-glutamyl-L-cystine.

EXAMPLE 5

A cream having the following composition was prepared.

Composition 5

| | | |
|---|---|---|
| (1) | Beeswax | 4.0 g |
| (2) | Cetanol | 5.0 g |
| (3) | Stearic acid | 5.0 g |
| (4) | Lanoline | 3.0 g |
| (5) | Pristane | 25.0 g |
| (6) | Polyoxyethylene (4) stearyl ether | 3.5 g |
| (7) | Glyceryl monostearate | 1.5 g |
| (8) | γ-L-glutamyl-L-cystine | 2.0 g |
| (9) | Propylene glycol | 10.0 g |
| (10) | Purified water | 41.0 g |
| (11) | Fragrance, preservative | suitable quantity |
| | | 100.0 g in total |

Method of Preparation

The aqueous layer ingredients (1) to (7) and the oily layer ingredients (8) to (11) were dissolved under heating at 80° C., respectively. Then, the oily layer mixture was gradually added to the aqueous layer mixture while they were emulsified in a homomixer. The mixture was stirred to make a homogeneous mixture. And the mixture was cooled to make a cream.

EXAMPLE 6

A cream having the following composition was prepared.

Composition 6

| | | |
|---|---|---|
| (1) | Beeswax | 4.0 g |
| (2) | Cetanol | 5.0 g |
| (3) | Stearic acid | 5.0 g |
| (4) | Lanoline | 3.0 g |
| (5) | Pristane | 25.0 g |
| (6) | Polyoxyethylene (4) stearyl ether | 3.5 g |
| (7) | Glyceryl monostearate | 1.5 g |
| (8) | γ-L-glutamyl-L-cysteine disulfide | 2.0 g |
| (9) | Propylene glycol | 10.0 g |
| (10) | Purified water | 41.0 g |
| (11) | Fragrance, preservative | suitable quantity |
| | | 100.0 g in total |

Method of Preparation

A cream was obtained by mixing and treating the above ingredients in accordance with the formulation similar to that of Example 5 except that γ-L-glutamyl-L-cysteine disulfide was used instead of γ-L-glutamyl-L-cystine.

EXAMPLE 7

A cream having the following composition was prepared.

Composition 7

| | | |
|---|---|---|
| (1) | Beeswax | 4.0 g |
| (2) | Cetanol | 5.0 g |
| (3) | Stearic acid | 5.0 g |
| (4) | Lanoline | 3.0 g |
| (5) | Pristane | 25.0 g |
| (6) | Polyoxyethylene (4) stearyl ether | 3.5 g |
| (7) | Glyceryl monostearate | 1.5 g |
| (8) | Oxidized glutathione | 2.0 g |
| (9) | Propylene glycol | 10.0 g |
| (10) | Purified water | 41.0 g |
| (11) | Fragrance, preservative | suitable quantity |
| | | 100.0 g in total |

Method of Preparation

A cream was obtained by mixing and treating the above ingredients in accordance with the formulation similar to that of Example 5 except that oxidized glutathione was used instead of γ-L-glutamyl-L-cystine.

EXAMPLE 8

A cream having the following composition was prepared.

Composition 8

| | | |
|---|---|---|
| (1) | Beeswax | 4.0 g |
| (2) | Cetanol | 5.0 g |
| (3) | Stearic acid | 5.0 g |
| (4) | Lanoline | 3.0 g |
| (5) | Pristane | 25.0 g |
| (6) | Polyoxyethylene (4) stearyl ether | 3.5 g |
| (7) | Glyceryl monostearate | 1.5 g |
| (8) | N,N'-diacetyl oxidized glutathione | 2.0 g |
| (9) | Propylene glycol | 10.0 g |
| (10) | Purified water | 41.0 g |

-continued

| (11) Fragrance, preservative | suitable quantity |
|---|---|
| | 100.0 g in total |

Method of Preparation

A cream was obtained by mixing and treating the above ingredients in accordance with the formulation similar to that of Example 5 except that N,N'-diacetyl oxidized glutathione was used instead of γ-L-glutamyl-L-cystine.

What is claimed is:

1. A whitening composition comprising
   (a) a compound selected from the group consisting of:
      (i) γ-L-glutamyl-L-cystine,
      (ii) γ-L-glutamyl L-cysteine disulfide,
      (iii) oxidized glutathione,
      (iv) γ-L-glutamyl-L-cystine acylated at the amino group with a straight or branched, saturated or unsaturated, alkanoyl group containing 1 to 20 carbon atoms, or with a benzoyl or naphthoyl group,
      (v) γ-L-glutamyl-L-cysteine disulfide acylated at the amino group with a straight or branched, saturated or unsaturated, alkanoyl group containing 1 to 20 carbon atoms, or with a benzoyl or naphthoyl group, and
      (vi) oxidized glutathione acylated at the amino group with a straight or branched, saturated or unsaturated, alkanoyl group containing 1 to 20 carbon atoms, or with a benzoyl or naphthoyl group,
   wherein said compound is present at a concentration of 0.001-10% (W/W); and
   (b) a cosmetically acceptable component.

2. The whitening composition according to claim 1, in which the cosmetically acceptable component is selected from the group consisting of a fat, an oil, a hydrocarbon, a wax, a fatty acid, a synthetic ester, an alcohol, a surfactant, a thickener, a moisturizer, a preservative, a pigment and a fragrance.

3. The whitening composition according to claim 1, in which the cosmetically acceptable component is a chemical selected from the group consisting of wheat germ oil, vitamin E, vitamin A, vitamin B2, magnesium ascorbic acid-2-phosphate, D-pantothenyl alcohol and dipotassium glycyrrhizinate.

4. The whitening composition according to claim 1 wherein said cosmetically acceptable component comprises:
   (a) 0.1%-30% (W/W) of a fat, oil, hydrocarbon, wax, fatty acid and synthetic ester, collectively;
   (b) 0.1%-25% (W/W) of an alcohol;
   (c) 0.1%-5% (W/W) of a surfactant;
   (d) 0.1%-0.5% (W/W) of a thickener;
   (e) 0.1%-25% (W/W) of a moisturizer;
   (f) 0.1%-0.3% (W/W) of a preservative;
   (g) 0.1%-1% (W/W) of a pigment;
   (h) 0.1%-5% (W/W) of a chemical;
   (i) a fragrance;
   (j) water; and
   (k) a cosmetically acceptable carrier.

5. The whitening composition according to claim 1 wherein said compound is N,N'-diacetyl-oxidized glutathione.

6. The whitening composition according to claim 4 wherein said compound is N,N'-diacetyl-oxidized glutathione.

7. A method of whitening the skin comprising the step of applying to the skin a cosmetic whitening composition which comprises a compound selected from the group consisting of:
   (a) γ-L-glutamyl-L-cystine;
   (b) γ-L-glutamyl L-cysteine disulfide;
   (c) oxidized glutathione;
   (d) γ-L-glutamyl-L-cystine acylated at the amino group with a straight or branched, saturated or unsaturated alkanoyl group containing 1 to 20 carbon atoms, or with a benzoyl or naphthoyl group,
   (e) γ-L-glutamyl-L-cysteine disulfide acylated at the amino group with a straight or branched, saturated or unsaturated, alkanoyl group containing 1 to 20 carbon atoms, or with a benzoyl or napthoyl group, and
   (f) oxidized glutathione acylated at the amino group with a straight or branched, saturated or unsaturated, alkanoyl group containing 1 to 20 carbon atoms, or with a benzoyl or napthoyl group.

8. The method according to claim 7 wherein said compound is N,N' diacetyl-oxidized glutathione.

* * * * *